(12) United States Patent
Talpo

(10) Patent No.: US 6,547,713 B1
(45) Date of Patent: Apr. 15, 2003

(54) THERAPY DEVICE USING VARIABLE MAGNETIC FIELDS

(75) Inventor: Getullio Talpo, Padua (IT)

(73) Assignee: S.I.S.T.E.M.I. S.r.l., Trento (IT)

( * ) Notice: Subject to any disclaimer, the term of this patent is extended or adjusted under 35 U.S.C. 154(b) by 0 days.

(21) Appl. No.: 09/762,255

(22) PCT Filed: Jul. 23, 1999

(86) PCT No.: PCT/EP99/05291

§ 371 (c)(1),
(2), (4) Date: Feb. 5, 2001

(87) PCT Pub. No.: WO00/07664

PCT Pub. Date: Feb. 17, 2000

(30) Foreign Application Priority Data

Aug. 4, 1998 (IT) .......................................... PD98A0191

(51) Int. Cl.⁷ .............................. A61N 2/00; A61N 1/08
(52) U.S. Cl. .............................................. 600/9; 607/59
(58) Field of Search ............................. 307/91; 600/13, 600/9, 14; 335/299; 128/921, 898

(56) References Cited

U.S. PATENT DOCUMENTS

| | | | | |
|---|---|---|---|---|
| 4,672,951 A | * | 6/1987 | Welch | 600/14 |
| 5,000,178 A | * | 3/1991 | Griffith | 600/13 |
| 5,010,897 A | * | 4/1991 | Leveen | 600/13 |
| 5,045,050 A | * | 9/1991 | Liboff et al. | 600/14 |
| 5,078,674 A | * | 1/1992 | Cadwell | 335/299 |
| 5,224,922 A | * | 7/1993 | Kurtz | 128/898 |
| 5,412,564 A | * | 5/1995 | Ecer | 128/921 |
| 5,437,600 A | * | 8/1995 | Liboff et al. | 600/9 |
| 5,441,495 A | * | 8/1995 | Liboff et al. | 600/13 |
| 5,465,012 A | * | 11/1995 | Dunnam | 307/91 |
| 5,634,939 A | | 6/1997 | Kuster et al. | |
| 6,290,638 B1 | * | 9/2001 | Canedo et al. | 600/9 |

FOREIGN PATENT DOCUMENTS

| | | | | |
|---|---|---|---|---|
| DE | A-41 35 325 | | 4/1993 | |
| DE | 4235571 A1 | * | 4/1994 | ............ A61N/2/02 |
| DE | A-196 333 23 | | 4/1998 | |
| EP | A-0 625 361 | | 11/1994 | |
| WO | A-96 11723 | | 4/1996 | |
| WO | A-97 46277 | | 12/1997 | |

* cited by examiner

Primary Examiner—Eric F. Winakur
Assistant Examiner—Nikita R Veniaminov

(57) ABSTRACT

An apparatus for treating the human body with variable magnetic fields, which comprises an electrical waveform generator to be connected, through a cable, to Helmholtz coils, adapted to be moved close to the person to be treated, which produce low-intensity, low-frequency variable magnetic fields; an impedance meter with electrode terminals to be applied to the person to evaluate the effectiveness of the waves of the generator; and an electronic processing unit for controlling the waveform generator as a function of the measurements of the impedance meter and of memory parameters stored in the processing unit.

14 Claims, 1 Drawing Sheet

THERAPY DEVICE USING VARIABLE MAGNETIC FIELDS

BACKGROUND OF THE INVENTION

The present invention relates to an apparatus for treating human body with variable magnetic fields.

As it is known, human body, when subjected to an external magnetic field, can be considered to be constituted by ordered substructures which, from the point of view of magnetic induction, can be para-dia-ferro-antiferromagnetic.

A multiplicity of molecular aggregates are dispersed in the body; among these, the paramagnetic ones dispersed in glassy matrices are described in scientific literature where the behavior thereof is assumed to be illustrated.

These aggregates, an example of which is europium sulfide, are not in the condition of achieving from the point of view of the alignment of their "molecular spins" with external magnetic fields, i.e. the minimum energy condition, and show abnormal behaviors with respect to common paramagnetic materials.

These molecular aggregates are known in the art as "spin glasses" and in them owing to complex reasons magnetic susceptibility differs from that in accordance with Curie's law which describes variations in the susceptibility of a paramagnetic material as a function of the temperature.

As a matter of fact, for "spin glasses" below a temperature t(g), which is characteristic for each species, the magnetic moments of the material can no longer follow the variations of the applied magnetic field, whereas at temperatures higher than t(g) the susceptibility curves rejoin the curve extrapolated according to Curie's law.

The susceptibility value of tested samples is at its maximum at the temperature t(g) and if the applied field decreases in this interval the maximums become sharper.

Accordingly, it will be noted that at one well-defined temperature all the magnetic moments should cease to respond to variations of the magnetic field, this behavior being similar to cooperative behaviors typical of phase transitions.

An interesting characteristic of "spin glasses" is that below temperature t(g) the value of magnetic susceptibility becomes stabilized owing to fluctuation-dissipation processes due to processes exchange of kinetic energy between a system and the medium in which it is immersed, according to many states of equilibrium corresponding to energy levels very close to each other, which cannot be described individually but define a precise topological structure of the space which can be defined mathematically as "ultrametric", because it is similar in configuration to a family tree.

Moreover, one can state that the multiple states of equilibrium mentioned above can be associated with general characteristics concerning other parameters of static-dynamic equilibrium regarding the entire matrix of the specimen system and these states can be considered essentially as "associative memories", i.e. regarding the systemic evolution of an object being considered.

In particular, this static-dynamic equilibrium is associated with precise values of resonance of the "molecular spins" of the subsets that constitute the entire system "versus" external magnetic fields characterized in terms of intensity, frequency and shape.

Assuming that parts of living beings behave like "spin glasses" at a "magnetic freezing" temperature of about 37° C., it is possible to make the effectiveness of variable magnetic fields known as E.L.F., i.e. fields characterized by low intensity (up to a few Gauss) and low frequency (of the order of ten Hertz) to correspond to the "spin" resonances induced on the biological complexes that constitute the body, which have the effect of modifying even permanently the ongoing physiological processes.

In this respect, E.L.F. fields can interact with body homeostasis, defined as a dynamically characterized sum of organic actions suitable for the preservation of life with respect to both external events for a living subject (color, sounds, lights, etc.) and internal events (aging, present or past diseases, etc.), these actions inherently fluctuating according to rhythms known as "Circadian".

In view of these premises, apparatus for treating human body with magnetic fields are currently widely used and essentially merely irradiate the human body with E.L.F. magnetic fields, assuming simplistically that this can lead to beneficial effects without, however, having objective evidence that such effects are developing or that the applied magnetic fields are the most suitable for a given person in order to achieve the best results.

SUMMARY OF THE INVENTION

The aim of the present invention is thus to provide an apparatus for treating the human body with variable magnetic fields which allows treatments to be made which are diversified for each person and for each situation, while identifying which magnetic fields are the most appropriate and detecting any development of the beneficial effects during treatment.

Within the scope of the above aim, consequent primary object is to provide an apparatus arranged to perform both treatments of a standardized type on the base of any information gathered from the literature concerning average behaviors of individuals in different situations and personalized treatments for each individual.

Another important object is to provide an apparatus which can be controlled by a computer.

This aim, these objects and others which will become better apparent hereinafter are achieved by an apparatus for treating the human body with variable magnetic fields, characterized in that it comprises:

at least one electric waveform generator to be connected, through a cable, to Helmholtz coils known per se (to be moved close to a person to be treated) which produce low-intensity, low-frequency variable magnetic fields (known as E.L.F.);

at least one impedance meter having electrode terminals to be applied to the person to evaluate the effectiveness of the waves of said generator;

at least one electronic processing unit for controlling said at least one waveform generator as a function of the measurements of said at least one impedance meter and of memory parameters stored in said processing unit.

Advantageously, at least one SMART CARD reader with an EEPROM memory can be provided for transmitting personal parameters concerning previous treatment sessions or parameters deemed at the outset more suitable for a person to be treated to said at least one processing unit.

BRIEF DESCRIPTION OF THE DRAWINGS

Further features and advantages of the invention will become better apparent from the detailed description of an embodiment thereof, illustrated only by way of non-limiting example in the accompanying drawings, in which the sole Figure is an electrical block diagram of the apparatus.

DESCRIPTION OF THE PREFERRED EMBODIMENTS

Figure 1:
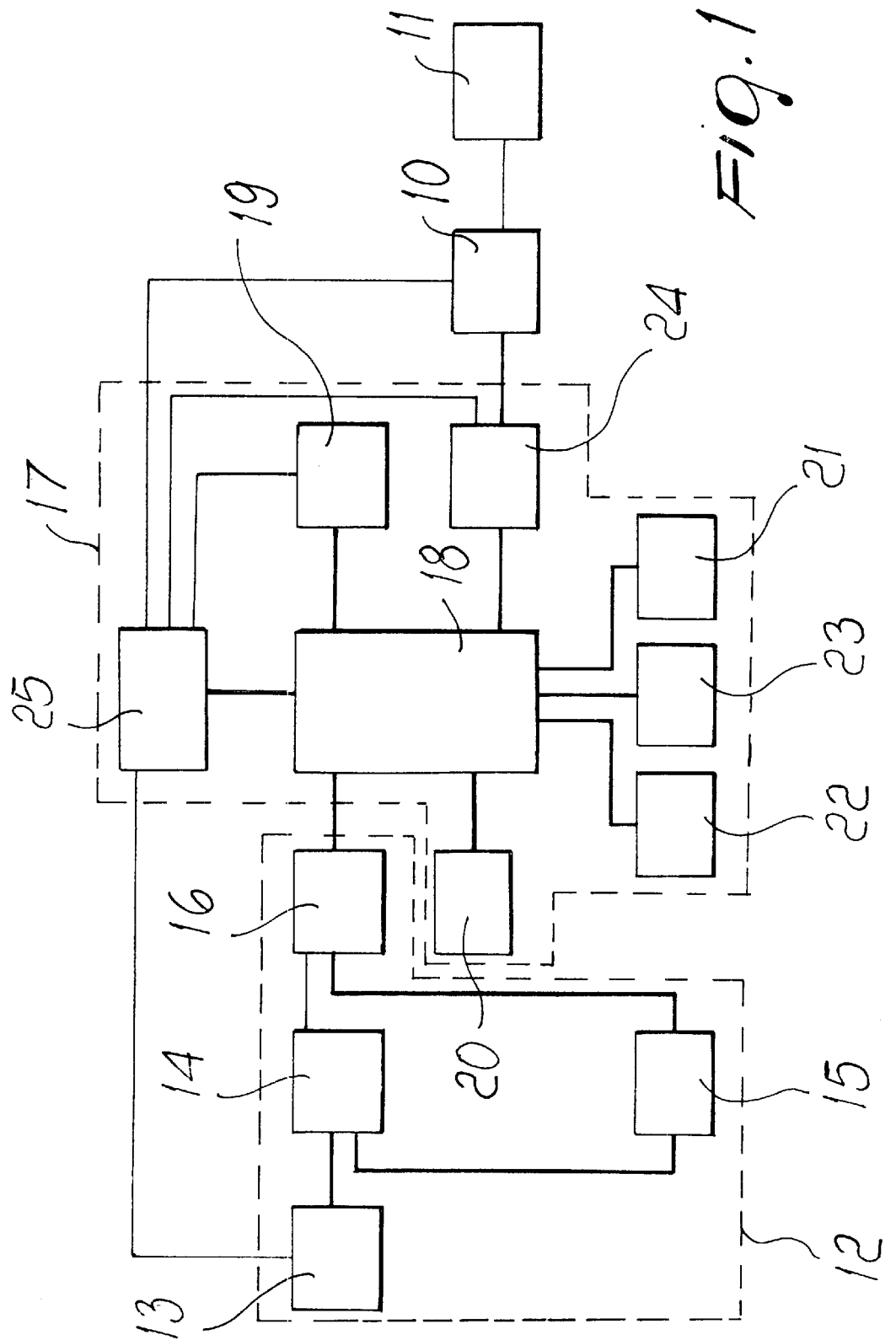

With reference to the above Figure, an apparatus for treating the human body with variable magnetic fields comprises a DAC electrical waveform generator, designated by the reference numeral 10, to be connected through a cable to Helmholtz coils, designated by a block 11.

The output of the DAC generator is conditioned and attenuated by a 100 steps software-controlled digital potentiometer, not shown, so as to vary the intensity of the out signal controlling the coils 11.

Power signals are forwarded to the output connector through a relay, not shown, which is used to reverse the magnetic field generated by the coils 11.

The coils 11 produce variable low-intensity, low-frequency magnetic fields known as E.L.F.

Furthermore, the apparatus comprises an impedance meter, generally designated by the reference numeral 12, which is constituted by a 50-Hz, 250-microampere (RMS) sinusoidal current generator 13 coupled to a sine generator 14 and provided with electrode terminals 15 to be applied to a person being treated.

The terminals 15 are preferably four in number and are designed to be applied to the hands and feet of a person.

The current generator 13, the sine generator 14 and the terminals 15 are connected to an impedance meter 16 which measures the phase shift of the sine wave with respect to both the X axis and the Y axis, after the current is passed through the human body.

The phase shift data indicate the resistance and reactance value, respectively, of a person being treated and their time evolution, when the person is subjected to magnetic fields, is taken as a basic reference for controlling the treatment.

The sine generator 14 is frequency-locked by means of a PLL to a forced signal generated by the logic unit and the signal is sent to the generator 13.

The voltage across the impedance constituted by the human body is applied to two synchronous demodulators which produce an analog output voltage proportional to the resistance and reactance of the applied load.

The apparatus according to the invention also comprises an electronic control processing unit, generally designated by the reference numeral 17 and comprising a microprocessor 18, e.g. an 87C552 with a series of peripheral units, such as an alphanumeric LCD display 19, a RAM-PROM memory, designated by the reference numeral 20, e.g. of the 8-bit 32-Kbyte type for the RAM part and of the 8-bit 64-Kbyte type for the PROM part, a keyboard 21, a SMART CARD reader 22, a UART circuit 23 with an RS232 serial interface, a DUAL-PORT memory designated by the reference numeral 24, e.g. of the 8-bit 2-Kbyte type.

The keyboard 21 is controlled by a chip (74C922) which eliminates any key rebounds, provides an interrupt to the microprocessor 18 at each keypressing and stores the key value which is then retrieved even after release.

The DUAL-PORT memory 24 constitutes a data buffer between the microprocessor 18 and the DAC generator 10.

Once the memory has unloaded the data of the required waveform into the buffer, said data are forwarded to the generator 10 by means of an address generator whose timing is directly controlled by the microprocessor 18.

The hardware-generated clock of the microprocessor has a variable rate, so as to obtain the waveform at a set frequency.

All the listed peripheral units (except the SMART CARD reader 22 and the UART circuit interface) are I/O-mapped through a PAL (22U10) designated by the reference numeral 25.

An additional PAL (ISPLSI 2032), again designated by the reference numeral 25, is used as an address generator for the DUAL-PORT memory, as a divider to provide 200 KHz to the impedance meter 16, and as base decoder.

The SMART CARD reader 22, which implements an EEPROM memory in IIC BUS technology, is connected via a connector to a control POLLING memory, thereby detecting the presence of the SMART CARD through a CARD PRESENT contact.

Besides controlling the peripheral units, the microprocessor 18 measures the analog values of the impedance and the resistance of the human body at the current intensity of the current passing through the coils 11 used to generate the magnetic field.

An internal 10-bit resolution ADC circuit is used for these measurements.

The above described apparatus is arranged to detect the spot values of some magnetic resonances of the organic complexes in the body of a person being treated, in order to modify them through application of specific pulsated and modulated magnetic fields most favourable to the health of that person.

Since the state of equilibrium of a patient at the treatment time is inherently unknown, a system for detecting the patient's sensitivity to external pulsated magnetic fields comprises measuring the variations of other physical parameters of his body while being stimulated by a plurality of external magnetic fields.

In a circuit comprising unknown capacitors and resistors (such as the human body can be considered to be), it is possible to measure the overall values of these parameters by applying thereto a sinusoidal current and, by measuring the wave phase shift with respect to both the X axis and the Y axis, it is possible to obtain the global values of the capacity and resistance, respectively.

According to a well-recognized model in the field of medicine and biophysics, whereas the values of resistivity of body liquids, in proportion to the dispersion of the ionic elements present therein, contribute to the total body resistance, the complex of the cells, considered as capacitors characterized by the osmotic membrane potential, constitute the imaginary part of the impedance (reactances).

Briefly stated, a modeling of the human body is assumed to be comparable to an RLC circuit in parallel having a negligible inductive component.

By immersing a person in diversified sequences of modulated E.L.F. magnetic fields, i.e. variable in terms of shape, intensity and frequency, when a particular sequence is resonant with the structure of an ordered part of the body or of the entire body, the reactance and resistance values thereof are modified.

Since multiple modulated wave trains can modify these configurations, it is possible, on the ground of a long established practice, to identify those capable of modifying more favorably the general state of health of the person.

This evaluation is also assisted by safe notions concerning both the significance of the measured impedance values on the human body and the (empirically) measured effect of some specific E.L.F. fields on living beings.

As far as the operation of the apparatus is concerned, first a 50-KHz, 250-microampere sinusoidal current is applied to the person through the electrode terminals 15 and its phase shift on the X axis and the Y axis after passing through the body is measured.

The two data which represent the resistance and reactance values, respectively, of the person are stored in their time evolution (when subjected to magnetic fields) in the digital memory.

The microprocessor 18 is arranged to send control signals to the DAC generator, which produces preset electric pulses which, by being transmitted via a cable connected to the coils 11, generate E.L.F. magnetic fields.

The control signals from the microprocessor 18 program different sequences of electromagnetic waves which are variable and can be modulated in terms of intensity, frequency and waveform.

It is possible to use both a standardized procedure which resides in a program loaded in the microprocessor 18 and a dedicated procedure by reading the SMART CARD memory in the reader 22, or by means of the keyboard 21 and, finally, by means of a suitable external program computer which is connected to the apparatus through the serial interface connected to the UART circuit 23.

The electrodes can be applied to the person to be treated so that two of them are located in the hand region and two in the foot region.

Initially, the field in the Helmholtz coils is absent, so that the apparatus can read and store the initial impedance value of the subject.

On the basis of this value, and possibly by taking advantage of mathematical algorithms, the microprocessor 18 will interpret some parameters concerning the state of health of the patient and it extrapolates discrete operating values of the E.L.F. field intensity.

A set of waves stored in the digital memory (for example 30) is grouped into subfamilies (for example five), each of which contains a series of waveforms (for example six); after some time, the first wave of each subfamily is obtained, modulated and varied according to discrete frequencies and then transmitted to the coils 11 in order to apply the corresponding magnetic field to the person being treated.

At the same time, at regular time sequences, the resistance and reactance values associated with the generated waves are read and stored.

At the end of this operation, the microprocessor 18, by comparing the stored values, is in a position of taking a series of decisions regarding a treatment cycle.

Once the cycle has ended, the apparatus, by means of the display 19, requests a SMART CARD to be inserted in the reader 22 to store therein the extracted procedures.

As an alternative, the apparatus can be connected to an external computer, as mentioned above, and can therefore be controlled by means of a suitable program.

The person to be treated is moved close to the Helmholtz coils 11 and the electrodes 15 thereof are applied for impedance measurements.

The monitor of the computer displays, optionally in a graphic procedure, the variation in resistance and reactance produced by the application of various selected wave trains in addition to the diagnostic parameters connected to the impedance measurement.

Finally, the data are stored in a suitable file.

Then, after reading the data by means of other diagnostic programs concerning the impedance measurements, it is possible to store the data of a SMART CARD for subsequent use.

The SMART CARD, whether stored in the first or in the second manner, when inserted into the apparatus, subsequently provides the microprocessor with the instructions for continuing the treatment.

In the first case, the instructions are for modulating and varying over a discrete frequency and intensity range the elements that consist of the waveforms that form the family that was determined to be the most suitable one, whereas the treatment time can remain fixed in a standard manner.

In the second case, the SMART CARD provides the processor with the times, waveforms, frequencies and intensities that have been selected, e.g. by an expert who has evaluated them and read them according to experience or studies on the subject.

It should also be noted that the apparatus can also be used simply for applying variable magnetic fields to the person being treated without having a confirmation from the impedance meter 12.

In this case, with the keyboard 21 and by means of instructions visible on the display 19, it is possible to select one of a series of waveforms stored in the digital memory, select its frequency, the duration of the treatment in minutes, the height of the electric pulse that generates the magnetic field on the coils 11.

In practice, it was found that the intended aim and objects of the present invention have been achieved.

As a matter of fact, an apparatus for treating the human body with variable magnetic fields has been provided which allows treatments diversified for each person and, for a same person, for each situation, while identifying which magnetic fields are the most suitable and detecting the development of the beneficial effects during the treatment.

Furthermore, the apparatus, possibly controlled by a computer, can perform treatments of a standardized type on the ground of experience possibly gathered in the literature in relation to the average behaviors of individuals in different situations and treatments which are personalized for each individual.

The invention as described above is susceptible to numerous modifications and variations, all of which are to be considered as falling within the scope of the appended claims.

The disclosures in Italian Patent Application No. PD98A000191 from which this application claims priority are incorporated herein by reference.

What is claimed is:

1. An apparatus for treating the human body with variable magnetic fields, comprising:
    at least one electric waveform generator to be connected through a cable, to Helmholtz coils, adapted to be moved close to a person to be treated, which produce low-intensity, low-frequency variable magnetic fields;
    at least one impedance meter having electrode terminals to be applied to the person to evaluate the effectiveness of the waves of said at least one generator;
    at least one electronic processing unit for controlling said at least one waveform generator as a function of the measurements of said at least one impedance meter and of memory parameters stored in said processing unit, and wherein said at least one electronic processing unit comprises a microprocessor with a RAM-PROM memory and a DUAL-PORT memory.

2. The apparatus according to claim 1, comprising a SMART CARD reader with an EEPROM memory for transmitting personal parameters concerning previous treatment sessions and/or parameters deemed at the outset more appropriate for the person to be treated to said processing unit.

3. The apparatus according to claim 2, wherein said processing unit comprises a serial interface for connection to an external control computer.

4. The apparatus according to claim 3, wherein peripheral units of said processing unit, except said SMART CARD reader and said interface, are I/O-mapped by means of a PAL.

5. The apparatus according to claim 4, wherein said PAL is used as an address generator for the DUAL-PORT memory, as a divider for supplying a frequency of 200 KHz to said impedance meter and as a base decoder.

6. The apparatus according to claim 1, wherein said processing unit is provided with a keyboard and a display for contributing in controlling said generator and said impedance meter.

7. The apparatus according to claim 1, wherein said impedance meter comprises a 50-Khz, 250-microampere (RMS) sinusoidal current generator and a sine-wave generator connected therewith.

8. An apparatus for treating the human body with variable magnetic fields, comprising:
   at least one electric waveform generator to be connected through a cable, to Helmholtz coils, adapted to be moved close to a person to be treated, which produce low-intensity, low-frequency variable magnetic, fields;
   at least one impedance meter having electrode terminals to be applied to the person to evaluate the effectiveness of the waves of said at least one generator;
   at least one electronic processing unit for controlling said at least one waveform generator as a function of the measurements of said at least one impedance meter and of memory parameters stored in said processing unit, and wherein said impedance meter comprises a 50-Khz, 250-microampere (RMS) sinusoidal current generator and a sine-wave generator connected therewith.

9. The apparatus according to claim 8, comprising a SMART CAD reader with an EEPROM memory for transmitting personal parameters concerning previous treatment sessions and/or parameters deemed at the outset more appropriate for the person to be treated to said processing unit.

10. The apparatus according to claim 9, wherein said processing unit comprises a serial interface for connection to an external control computer.

11. The apparatus according to claim 10, wherein peripheral units of said processing unit, except said SMART CARD reader and said interface, are I/O-mapped by means of a PAL.

12. The apparatus according to claim 11, wherein said PAL is used as an address generator for the DUAL-PORT memory, as a divider for supplying a frequency of 200 KHz to said impedance meter and as a base decoder.

13. The apparatus according to claim 8, wherein said processing unit is provided with a keyboard and a display for contributing in controlling said generator and said impedance meter.

14. The apparatus according to claim 8, wherein said at least one electronic processing unit comprises a microprocessor with a RAM-PROM memory and a DUAL-PORT memory.

* * * * *